United States Patent [19]

Lakin

[11] 4,271,707
[45] Jun. 9, 1981

[54] RECEIVED SIGNAL ENCODING AND CORRELATING SYSTEM

[75] Inventor: Kenneth M. Lakin, Palos Verdes, Calif.

[73] Assignee: Northrop Corporation, Los Angeles, Calif.

[21] Appl. No.: 95,576

[22] Filed: Nov. 16, 1979

[51] Int. Cl.³ .............................................. G01N 29/04
[52] U.S. Cl. ..................................................... 73/614
[58] Field of Search ................ 73/614, 615, 616, 626; 367/122, 123, 100

[56] References Cited

U.S. PATENT DOCUMENTS

| | | | |
|---|---|---|---|
| 3,775,734 | 11/1973 | Bealor et al. | 367/95 |
| 3,918,024 | 11/1975 | Macovski | 73/614 |
| 3,999,422 | 12/1976 | Lehmann et al. | 73/614 |
| 4,173,007 | 10/1979 | McKeighen et al. | 367/123 |

Primary Examiner—Anthony V. Ciarlante
Attorney, Agent, or Firm—William W. Rundle; Willard M. Graham

[57] ABSTRACT

An ultrasonic phased array imaging system having a received signal encoding and correlating system. Pulse echoes picked up by each of the plurality of transducers are passed by a timed gate signal only during a predetermined time interval when a return signal from a focal point is expected to arrive. The return signal is also encoded by a chirp waveform. All gated chirp signals are fed to a dispersive transversal filter where their sum occurs simultaneously.

13 Claims, 9 Drawing Figures

RECEIVED SIGNAL ENCODING AND CORRELATING SYSTEM

BACKGROUND OF THE INVENTION

1. Field of the Invention

The present invention relates to correlation of signals received by a phased array of transducers, and more particularly, to a signal encoding and decoding system for a phased array of transducers in a nondestructive ultrasonic inspection system.

Ultrasonic methods are in use today for testing for flaws in manufactured parts, wherein a single transducers is scanned back and forth across the area to be inspected. In the aircraft industry, graphite and/or other composite and laminated structures are coming into operational use, and these new composite materials entail additional inspection requirements. These requirements include high speed inspection of a multiplicity of drilled holes, high speed inspection of large areas and of new structural shapes which are difficult to inspect, and new field inspection demands after the aircraft are put into service.

In the pulse-echo mode, the ultrasonic transducer is coupled with the part being inspected and detects defects by scanning around each drilled hole or along the length and width of the formed component. That is, the transducer must physically "paint" the area requiring inspection.

Some multi-transducer approaches are coming into use and some even involve electronic scanning and steering. It is still a problem, however, to determine from the complex return signals received by the array just where the signals came from in the volume of material or space under consideration. In the phased array systems, the return signals will arrive at the transducers from a scattering point with various relative delay times dependent upon their distance from the scattering point. Since these signals overlap somewhat in time, they cannot be put into one single delay line and many separate variable delay lines for a multi-element array are very expensive.

The return signals, which are analog in nature, could each conceivably be converted to digital form before individual time delays were accomplished, but this would require expensive, fast-acting analog-to-digital coverters, one for each transducer.

2. Description of the Prior Art

U.S. Pat. No. 3,261,969 to Routh discloses an autocorrelation system for processing sonar signals, from one transducer input, which uses a dispersive delay line.

U.S. Pat. No. 3,158,830 to Clay, Jr. discloses an acoustic depth measurement system employing a signal correlation means with a rotating delay line, and another embodiment having matched filter means. This prior system correlates the return signal with a replica of the transmitted signal for the purpose of signal to noise improvement. Applicant's present invention does not correlate the received and transmitted signals but cross-correlates many received signals.

U.S. Pat. No. 3,918,024 to Macovski discloses an ultrasonic focused array imaging system employing variable delay lines. A system having a large number of necessarily complicated delay lines as outlined in this prior patent would be impractical. U.S. Pat. No. 4,005,382 to Beaver is somewhat similar.

U.S. Pat. No. 3,005,335 to Erdman is typical of several references which employ chirped waves for the purpose of measuring time delay wherein the chirp signals themselves are actually radiated and received. Such systems do not cross-correlate a plurality of received signals.

U.S. Pat. No. 3,639,695 to Bertheas is an example of radar or sonar systems having dispersive networks for signal compression.

U.S. Pat. No. 3,775,734 to Bealor, Jr. et al discloses a multi-channel sonar system which times the transmission sequence so that all sea floor echoes arrive back simultaneously at the receiving transducer.

U.S. Pat. No. 3,872,715 to Pittaro discloses an ultrasonic single-transducer test circuit using gates which open and close upon receipt of an echo signal.

While it is possible that more pertinent prior art exists, Applicant's search is believed to have been conducted with a conscientious effort to locate and evaluate the most relevant art available at the time, but this statement is not to be construed as a representation that no more pertinent art exists.

SUMMARY OF THE INVENTION

It is an object of the present invention to provide correlation of signals received by a plurality of ultrasonic transducers, electromagnetic antennas or signal paths.

It is a further object to provide an encoding and decoding system for return signals to an array of transducers so that any return signals from one given focus point received at different times by the multiple transducers are all summed simultaneously for output.

Another object is to help provide a high speed ultrasonic inspection system for aircraft components.

Briefly, my invention comprises a means and method for treating the return signals received by each transducer in a phased array so that all the respective transducer return signals from the instant focus point are summed and presented simultaneously, and return signals from other points are rejected. To this end, gate means are provided, one for each transducer channel, and means for causing said gate to be open only when it is time for a return signal (if any) to arrive from the focus point. Additionally, each transducer return signal is mixed with a time-dependent high frequency signal to identify the arrival time of that return signal at the transducer, and all such modulated pulses are fed to a common line. Then the composite signal on that line is fed to a dispersive transversal filter where all gated transducer signal pulses are collected and appear at the output simultaneously. Since all these transducer return signals are effectively added at the same time, a high signal-to-noise ratio is also achieved.

As to apparatus, I provide a coding chirped waveform branching to a separate gate or switch for each transducer return signal line, the coding chirp signal being gated for each transducer line by a gate pulse of predetermined width triggered by a trigger pulse from the transmitter control circuitry. The trigger pulse fed to each transducer gate is timed for that particular transducer to occur only when the return signal from the focal point is due to arrive. Each gated chirp pulse and the transducer return signal are fed to a mixer, one for each channel, and the mixer outputs are connected together. The combined mixer outputs are then fed to a decoding chirp line of exactly reverse frequency form from the coding chirp. The envelope of the decoding chirp line output is the Fourier transform of the plurality of return signals from the focal point which arrive back at the respective transducers at various times, but all being time-shifted to the same instant of output. Thus a high-strength signal is received in the presence of background "noise" and the like.

DESCRIPTION OF THE PREFERRED EMBODIMENT

The present invention will be described as incorporated in a particular example of an ultrasonic inspection system disclosed herein. It will be understood that this is for illustrative purposes only, in enabling a person skilled in the art to practice this invention.

Figure 1:
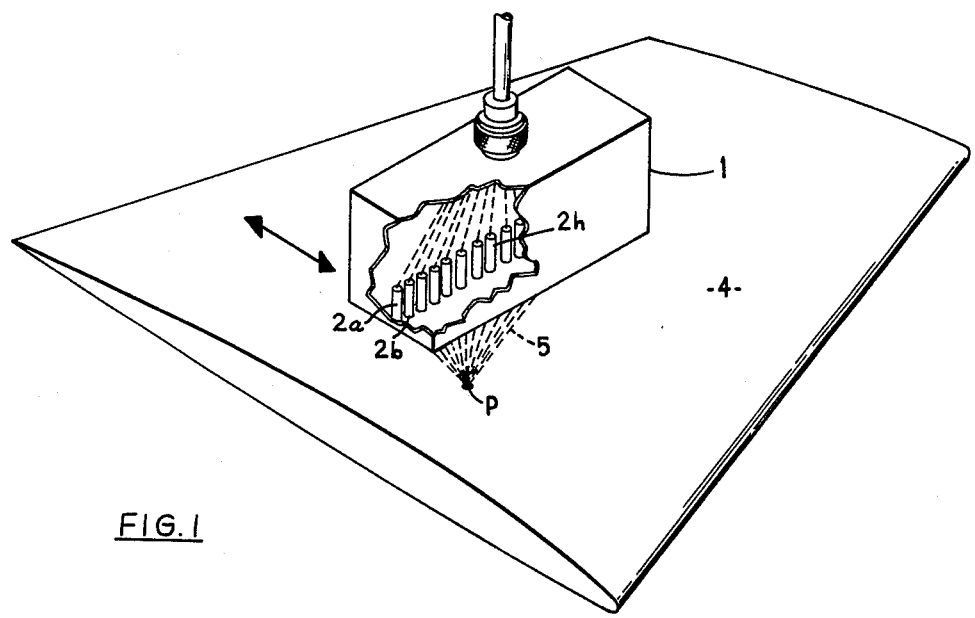
FIG. 1 is perspective view showing an array of ultrasonic transducers scanning an aircraft component during inspection for structural defects.

In FIG. 1, a scanning head 1 of an ultrasonic inspection system contains a linear array of 32, for example, piezo-electric transducers 2 positioned substantially even with an outer surface of the head 1 which is physically moved adjacent to one surface of an aircraft vertical stabilizer 4, for example, being inspected. As will be understood, the inspection process may be carried out under water or other liquid as a transmission medium for the ultrasonic waves. In some instances, the transducers 2 may physically touch the inspected material.

The particular system under consideration is an ultrasonic phased array system, i.e., a system wherein the transmitted signals form a "beam" 5 from the transducers 2, which beam is electronically steered. By suitably delaying the transmission of a pulse or short burst of ultrasonic energy from each respective transducer 2, the wavefront from each and every transducer may of course be made to arrive simultaneously at any predetermined point or small zone, such as point P in the stabilizer 4.

Figure 2:
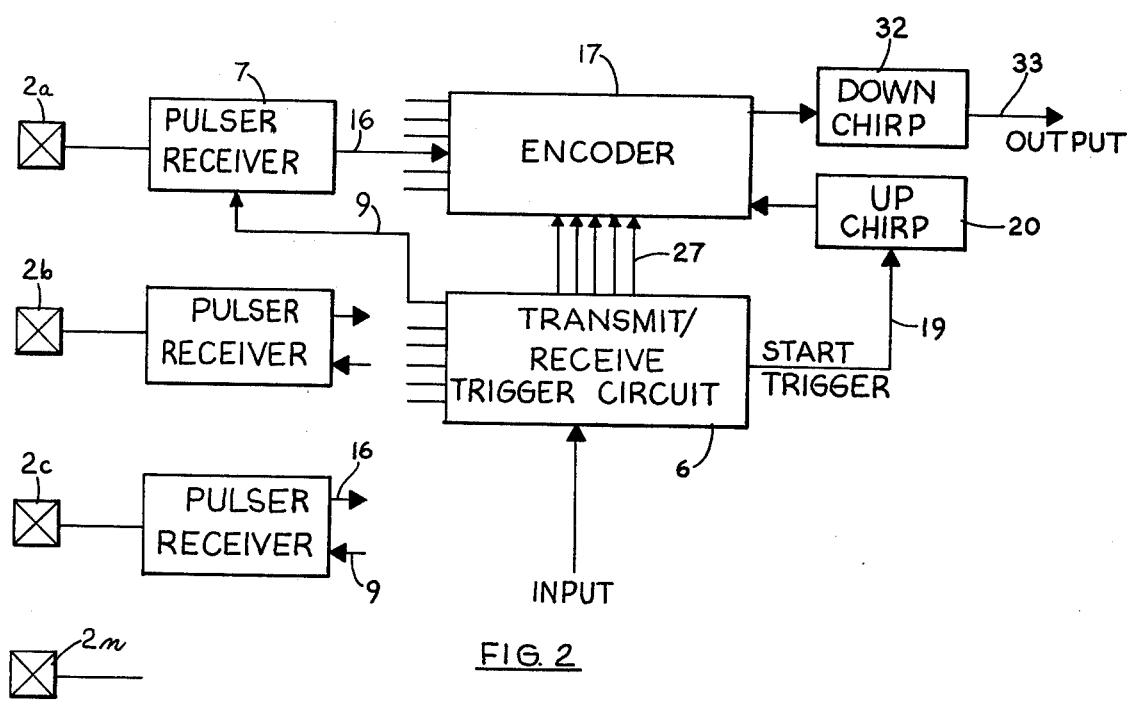
FIG. 2 is a block diagram of an ultrasonic phased array system incorporating the present invention.

FIG. 2 shows the overall inspection system electronics. Whenever an input signal pulse is fed to a transmit/receive trigger circuit 6, one transmit trigger pulse for each transducer 2 is relayed to a pulser/receiver unit 7 electrically connected to each transducer 2. In order to have the beam 5 focus at a point or small zone in the part being inspected, the transmit trigger pulse to each transducer 2 is respectively delayed the proper time to form the desired overall curved wavefront. Means for accomplishing this "transmit" delay in the transmit/receive circuit 6 is conventional, and will be discussed further later.

Figure 3:
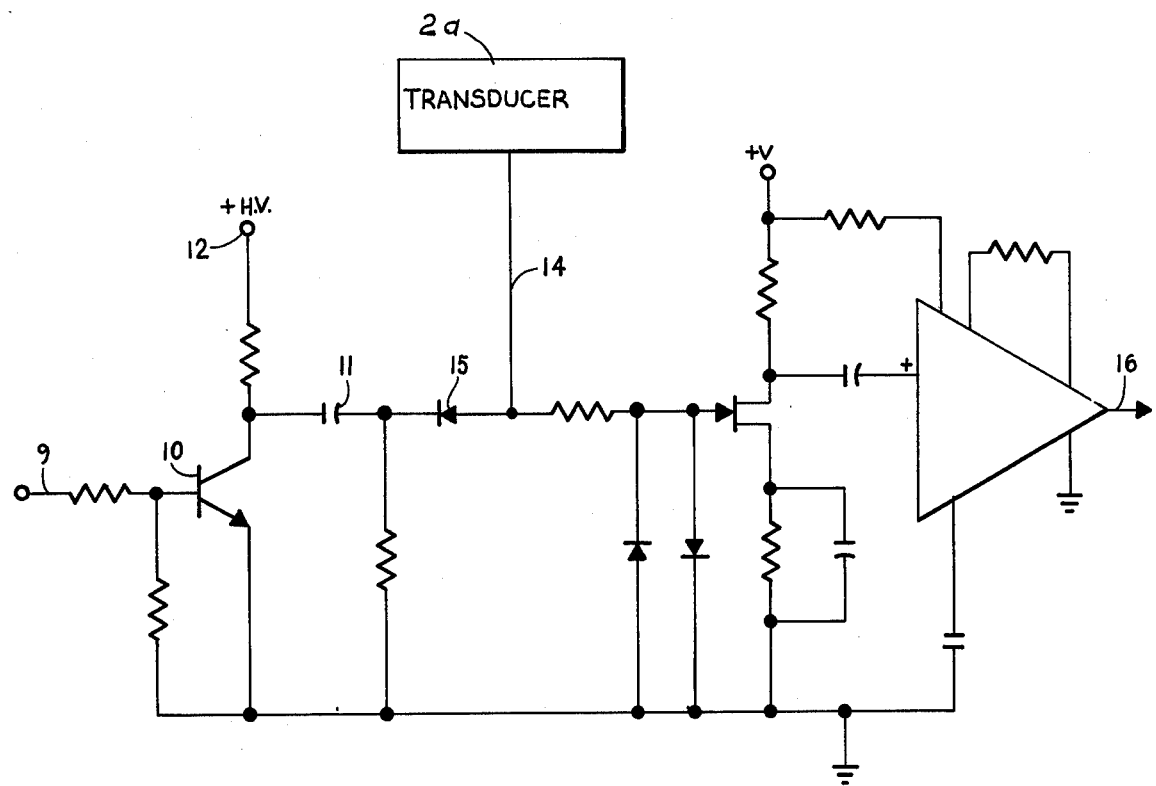
FIG. 3 is a schematic diagram of one pulser/receiver of FIG. 2.

One pulser/receiver 7 is shown in detail in FIG. 3, for example only. Here, the transmit trigger pulse occurs on a transmit trigger line 9 connected to the input of an avalanche transistor 10. A storage capacitor 11, previously charged from a high voltage terminal 12, is quickly discharged when the avalanche transistor 10 is turned on, and a very narrow excitation pulse is fed to the associated transducer 2a, for example, on a transducer feed line 14.

The transducers 2 are preferably designed to be "rung" by the high voltage pulse to produce a burst of approximately 2 to 2¼ MHz for about one microsecond. This produces a transmitted signal of about two cycles or less to be ultrasonically transmitted through the stabilizer 4 or other component being inspected.

As is well known, ultrasonic inspection systems look for reflections or return signals to indicate and/or display faults, discontinuities and the like. The present system desires to see if there are any return signals from the point P or not. Any reflections from any other point are to be disregarded or rejected.

The same feed line 14 carries return signals generated by the associated transducer 2a when reflected acoustic waves strike the transducer. Such return signals pass to the right from the blocking diode 15, are amplified and passed out of the pulser/receiver 7 on a receiver output line 16.

In this phased array system, the reflected signals from an anomaly at point P will arrive back at the transducers 2 with various relative delay times. They must then be collected and indicated at one time. Since these signals overlap somewhat in time they cannot be put into one single delay line, and N programmable delay lines for an N-transducer array is very costly. Thus, the encoding and decoding system of the present system was devised as an improved means of delaying and correlating the N signals. Return signals from the pulser/receivers 7 enter encoders 17 which are further shown in FIG. 4.

Figure 4:
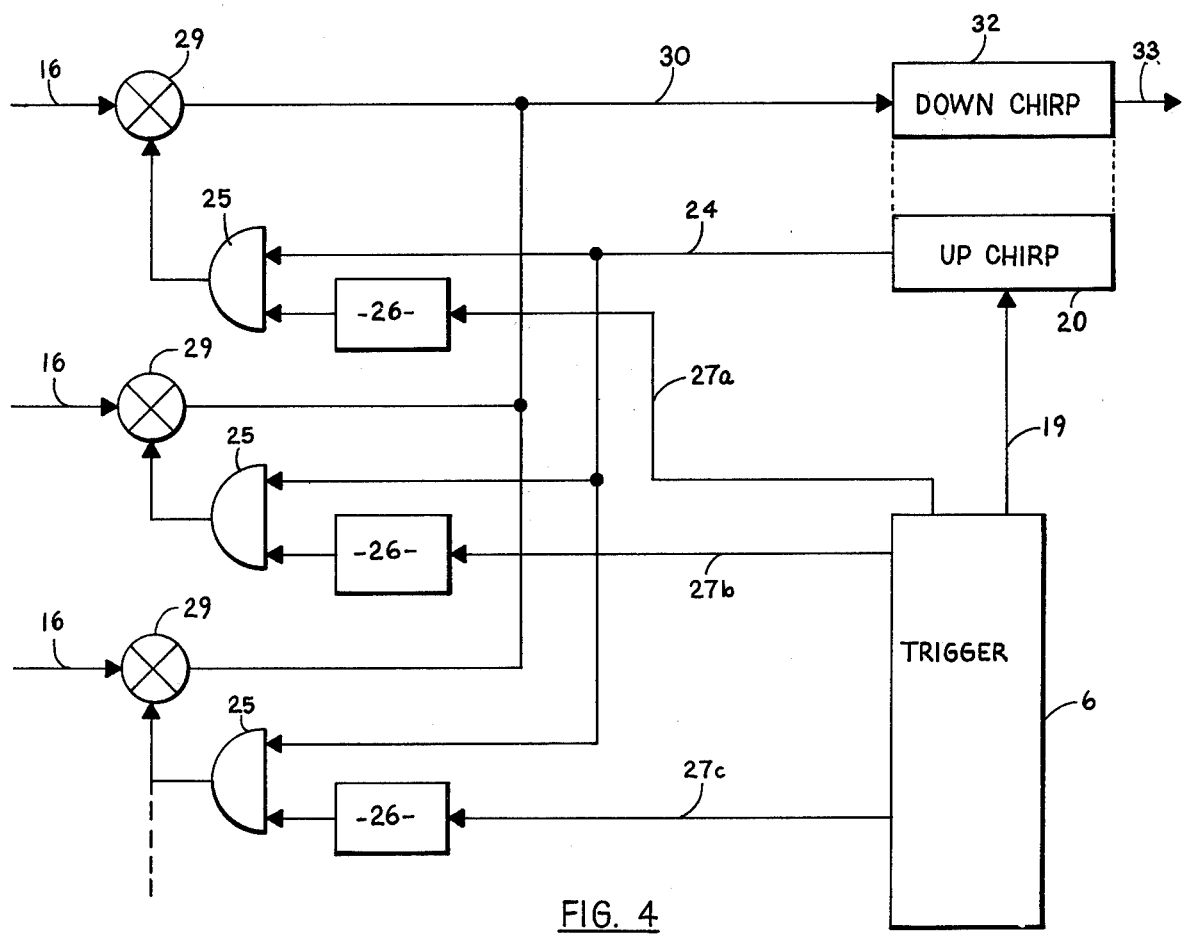
FIG. 4 is a block diagram showing details of the encoding portion of FIG. 2.

In FIG. 4, a reference trigger line 19 from the transmit/receive trigger circuit 6 connects to an up-chirp filter 20. The latter produces a chirp signal whose frequency varies with time in a monotonic manner. Such a device is common in radar technology, and may be designed to produce a chirp signal from 130 MHz to 180 MHz for example. The chirp waveform must last at least as long as the longest relative delay which may be about six microseconds for example.

The output of up-chirp filter 20 on a chirp output line 24 connects to one input of a plurality of gates 25 in parallel, one gate for each transducer 2. The second input of each gate 25 comes from the output of a one-shot multivibrator 26. The trigger input of each multivibrator 26 is respectively connected to an associated receive trigger line 27a, 27b, etc. for that particular gate circuit, coming from the transmit/receive trigger circuit 6.

The output of each gate 25 goes to one input of an associated signal mixer 29, preferably of the double balanced communications type. The other input of each signal mixer 29 connects from one of the respective receiver output lines 16 from the corresponding pulser/receiver 7. All signal mixer product outputs are connected to a common array output line 30 which is in turn connected to a down-chirp filter 32. The latter is a dispersive transversal filter, having a frequency versus time response which must be opposite to that of the up-chirp filter 20 used for encoding. The up-chirp and down-chirp filters 20 and 32 are preferably of the surface wave type. The output of the down-chirp filter 32 on a system output line 33 is the desired correlated return signal from the scattering point P in the component under test.

Figure 7:
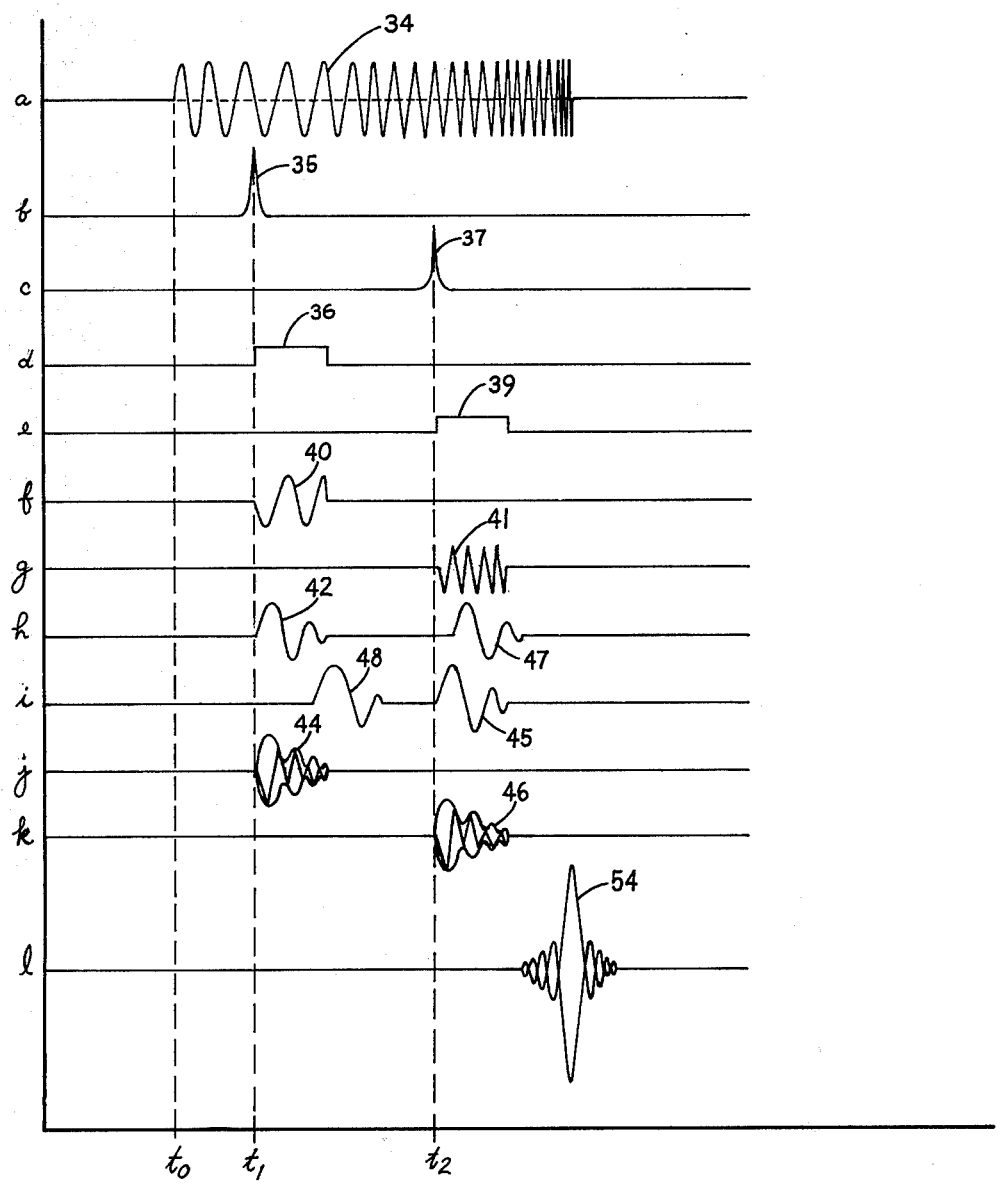
FIG. 7 is a timing diagram showing various signal waveforms used in describing operation of this invention.

In operation, the reference trigger line 19 carries a start pulse to the up-chirp filter 20 at a predetermined time slightly before the precomputed arrival time of the first return signal from the nearest transducer 2 to the point P. This start pulse causes the up-chirp filter 20 to produce a chirp waveform 34 as indicated on line a of the timing diagram of FIG. 7. FIG. 7 shows illustrative type signals which serve to explain the principles of the invention. As mentioned before, for this example, the length of the generated chirp waveform 34 is approximately six microseconds, starting at time $t_0$, for example.

At time $t_1$ a first delayed trigger pulse 35 on a first receive trigger line 27a arrives, as shown on line b of FIG. 7. This indicates a valid arrival time for the first transducer return signal to occur. The first trigger pulse 35 triggers its corresponding one-shot multivibrator 26 which produces a first gate signal 36 as shown on line d of FIG. 7. A second trigger pulse 37 on second receive trigger line 27b arrives at time $t_2$ as shown on line c of FIG. 7, timed to meet the start of occurrence of the second transducer return signal. This trigger pulse 37 likewise triggers its connected one-shot multivibrator 26 to produce a second gate signal 39 as shown on line e of FIG. 7. Similarly, all transducer channels have a properly delayed trigger pulse and gate signal.

All gate signals 36, 39 are identical in width, a little more than one microsecond in this example, to accommodate the reflected transmitted signal burst.

The outputs of the first two gates 25 are thus gated chirp signals 40 and 41, respectively, as shown on lines f and g of FIG. 7. It will be noted that their frequencies are slightly different, of course, depending on the frequency of the chirp waveform 34 at the time of gating.

The gates 25 may be diode switches, for example, or even double balanced mixers like the signal mixers 29.

All the gated chirp signals such as 40 and 41 go to their respective signal mixers 29 where they produce separate encoded array return signals in the signal mixer outputs. Each signal mixer output is therefore the transducer return signal, on the respective receiver output line 16, modulated by the corresponding gated chirp signal for the time period in which the gated chirp signal occurs. For example, a particular first transducer return signal 42 on line h of FIG. 7 which is coincident with the first time-gated chirp signal 40 appears in the signal mixer output as a particular first encoded array return signal 44 (line j of FIG. 7). Similarly, in another transducer channel, a second transducer return signal 45 (line i of FIG. 7) mixes with its gated chirp signal 41 to form a second encoded array return signal 46 (line k of FIG. 7).

If a return signal came to each transducer 2 from only the point or small zone P being focused upon, then the gates 25 would not be necessary. But the gates are used to eliminate echoes from discontinuities at points other than the small sampled volume represented by point P, and also from the top and bottom surfaces of the article under test. For instance, the two illustrative extraneous signals 47 and 48 on lines h and i, respectively, of FIG. 7, may be present as return signals to the transducers, but they are not time-gated through the signal mixers 29. It is only the return signals from the point P (or none at all) which are ideally admitted to the down-chirp filter 32 and thence to the system output.

Figure 5:
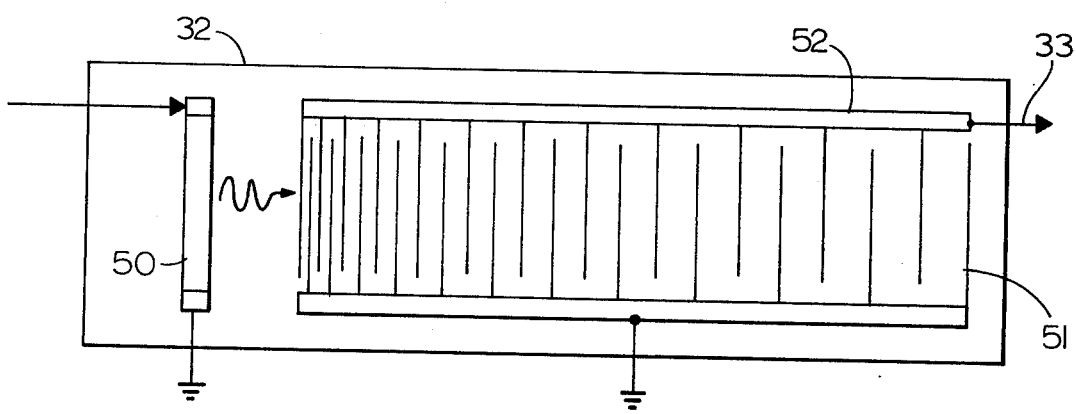
FIG. 5 is a pictorial diagram showing construction of a down-chirp line as used in FIG. 2.

On the array output line 30, all the encoded array return signals from one transmitted burst, such as return signals 44 and 46, are fed to the down-chirp filter 32, shown in more detail in FIG. 5. These electrical signals are applied at the left end to the input transducer section 50 and are changed to acoustic waves which propagate to the right. The output transducer section 51 is constructed of interdigitated electrodes such that its left end responds to high frequencies and regions to the right respond to progressively lower frequencies. Thus the high frequency signals pass with the least delay and the low frequency signals encounter the most delay.

During the encoding (FIG. 4) the first return signals were encoded by the low frequency portion of the chirp wave-form 34 and thus they undergo the longest delay during "decoding" in the down-chirp filter 32. While the first return signals are coming out of the output transducer section 51 at the right end, the later return signals are simultaneously coming out at the higher frequency portions toward the left end, and all are collected at the long output conductor 52 to which the system output line 33 is connected. All the transducer return signals are actually summed together and appear as a narrow, amplified output pulse 54, shown on line 1 of FIG. 7. Thus the two matched chirp lines 20 and 32 have performed the encoding and the correlating of the analog type array return signals.

Figure 6:
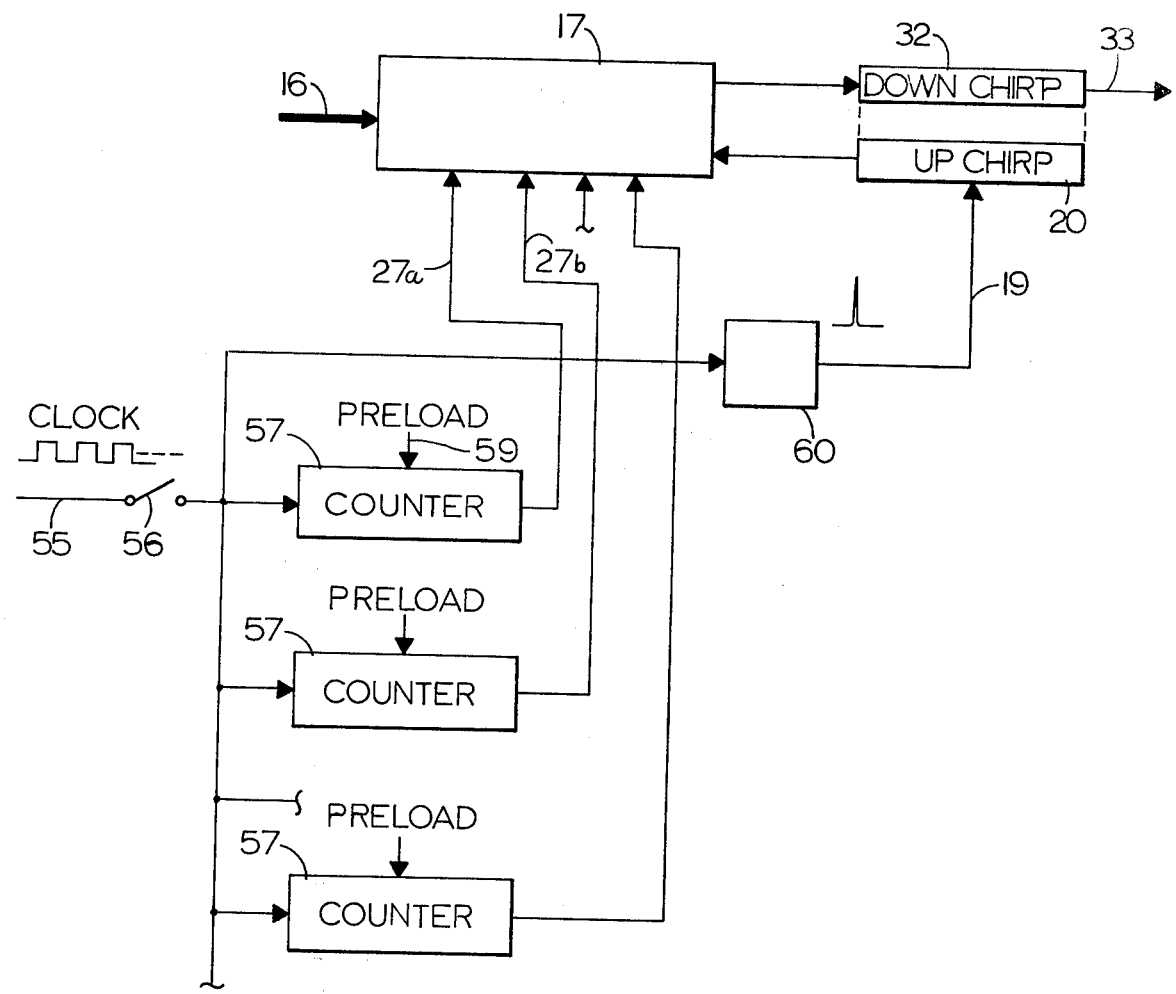
FIG. 6 is a block diagram showing one digital technique for providing the necessary individual delay times for encoding each transducer return signal.

As mentioned before, the opening of the gates 25 is timed so that only the transducer return signals from the single point of interest are accepted in the correlating system. For providing the required timing, the arrangement of FIG. 6 can be used in the transmit/receive trigger circuit 6 of FIG. 2. A control input line 55 carries a train of clock pulses to a control switch 56. Each time control switch 56 is closed to initiate a correlating cycle, a series of counters 57 is started, there being one counter for each transducer 2. Of course a correlating cycle refers to the activity following each transmitted burst from the array of transducers 2, when the return signals are received and correlated. The required time delay period for the return signal from the instant scattering point P to each transducer is pre-calculated and entered as a number on a preload line 59 to each respective counter 57. When each counter reaches the predetermined number of pulses counted, a carry pulse occurs at the counter output which goes to the encoders 17 on the aforesaid receive trigger lines 27. These carry pulses thus act as the respective trigger pulses to the one-shot multivibrators 26. The first clock pulse received by the counters 57 also goes to a single-pulse forming circuit 60 which sends a start trigger pulse on the reference trigger line 19 to the input of the up-chirp filter 20, thus starting the chirp waveform 34. When control switch 56 opens, the counters 57 will reset.

The above preload operation may be done manually or from a computer, and the preload number may be a constant or a variable. Other suitable fast-acting digital delay techniques could also be used. A similar arrangement may also be employed to provide the delays to the transmit trigger lines 9 of FIG. 2.

The present invention is not concerned with the correlated signal after it leaves the down-chirp filter 32. In the phased array system shown herein, the output signals will be fed to an analog-to-digital converter and may be stored in a computer memory for identification, comparison, display and the like.

Figure 8:
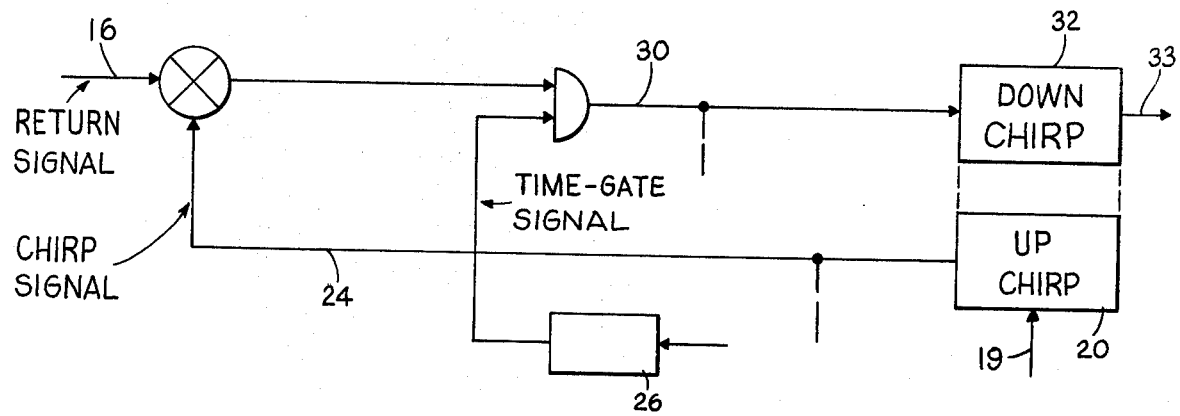
FIG. 8 is a partial block diagram showing an alternate signal mixing arrangement from that shown in FIG. 4.
Figure 9:
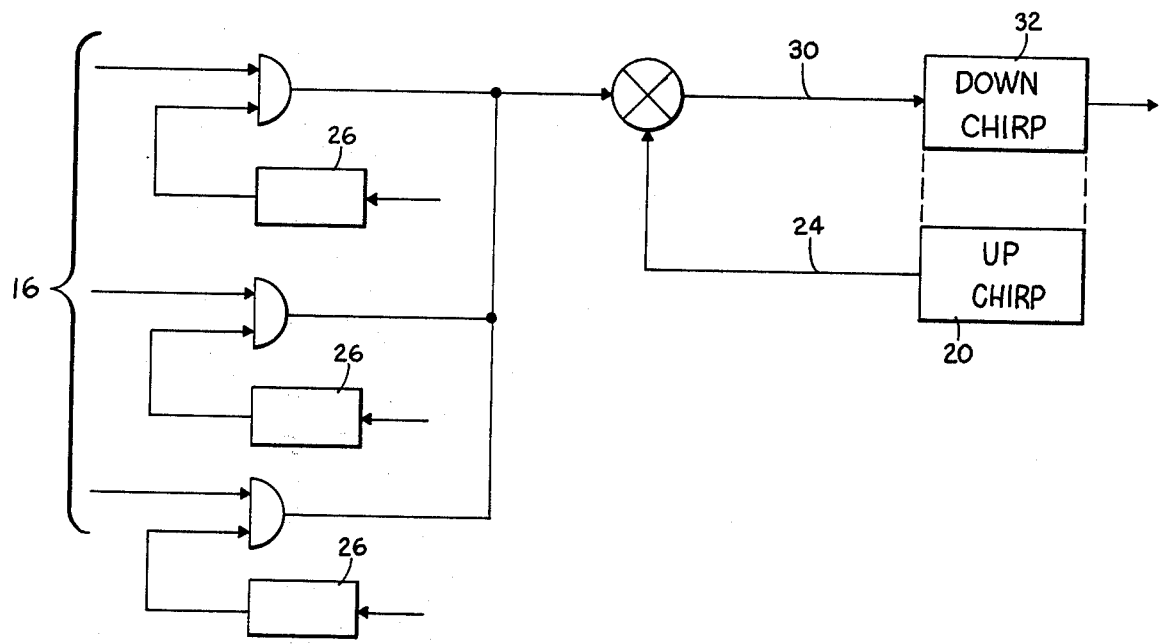
FIG. 9 is a partial block diagram showing a further signal mixing arrangement.

It is obvious that the up-chirp and down-chirp lines 20 and 32 may be reversed if desired, the only requirement being that they are matched in the sense of having exact opposite frequency curves. An alternate arrangement for the encoding structure of FIG. 4 is to mix the chirp signal 34 (on chirp output line 24) with the transducer return signals (on receiver output lines 16) before being time gated. This alternate arrangement is illustrated in FIG. 8, for one transducer channel only. Still another way is to time-gate the return signals first, combine the gated signals, and then mix the chirp waveform. This second alternate arrangement is illustrated in FIG. 9, showing a reduced circuit complexity. The key feature is to tag or label each transducer return signal in a way that uniquely indicates the delay required for the return signal to travel from point P to that particular transducer.

It is thus seen that a greatly improved correlating means has been provided for return signals received by an array of transducers. This method can be used anywhere a plurality of reflected signals or the like is received along different paths, in an imaging system for instance, whether the receiving elements are ultrasonic transducers, electromagnetic antennas, hydrophones in a sonar system, or other types. The transducer array may obviously be a one-dimensional or two-dimensional array where it is desired to bring into time coincidence a group of related signals from a certain scattering point for summing them simultaneously, thus achieving a high signal-to-noise ratio. The present invention finds use in mechanical or electronic scanning and steering of phased arrays. It eliminates the necessity for a bulky delay line in each transducer channel. For digital systems, this invention also makes it unnecessary to have a fast analog-to-digital converter in each transducer channel, since the down-chirp line 32 handles and brings together all the analog return signals.

While in order to comply with the statute, the invention has been described in language more or less specific as to structural features, it is to be understood that the invention is not limited to the specific features shown, but that the means and construction herein disclosed comprise the preferred mode of putting the invention into effect, and the invention is therefore claimed in any of its forms or modifications within the legitimate and valid scope of the appended claims.

What is claimed is:

1. In an ultrasonic pulse-echo inspection system wherein a pulse is transmitted from each of an array of transducers at slightly delayed intervals to arrive at a small focus zone or point simultaneously, the method of encoding, correlating, and decoding the respective return signals received by said transducers from said point which comprises:
    a. providing a chirp signal at least as long as the time required from the first to the last return signal received at said transducers;
    b. providing a gate signal for each transducer, said gate signal being timed to coincide with the predetermined arrival time of the return signal at its corresponding transducer;
    c. mixing said return, chirp and gate signals for each transducer by product means to form a time-gated chirp-modulated return signal for each transducer;
    d. combining all said time-gated chirp-modulated return signals from said transducers; and
    e. passing said combined signals through a dispersive transversal filter having a characteristic opposite to said chirp signal.

2. Method in accordance with claim 1 including time-gating said chirp signal by said gate signal, and mixing the resultant gated chirp signal with said return signal.

3. Signal correlation means for a plurality of transducers receiving return signals emanating simultaneously from a scattering point, comprising:
    a. means for generating a chirp signal varying unidirectionally in frequency with time;
    b. means for generating a gate signal of predetermined width and timing for each said transducer to coincide with the return signal at the associated transducer;
    c. mixer means for taking the product of said return, chirp and gate signals at each of said transducers; and
    d. means for obtaining the summation of said products simultaneously.

4. Apparatus in accordance with claim 3 wherein said summation means is a dispersive transversal filter having a frequency curve opposite to that of said chirp signal.

5. Apparatus in accordance with claim 3 wherein each said gate signal means comprises a trigger line for carrying a trigger pulse occurring at a precomputed time of return signal arrival at its associated transducer, and multivibrator means having its input connected to said trigger line and its output pulse width substantially equal to the time duration of the return signal.

6. In an acoustic imaging system wherein echo pulses from many points may be received by an array of transducers, means for correlating the return pulses received by said transducers from only one target point which comprises:
    a. mixer means for each said transducer, each said mixer means having two inputs and one output, a signal line connected from the corresponding transducer to one of said mixer inputs;
    b. gate means for each said mixer means, each said gate means having two inputs and one output, said gate means output connected to the second input of its corresponding mixer;
    c. a one-shot multivibrator for each said gate means, each said multivibrator having its output connected to one input of its corresponding gate means;
    d. separate trigger means connected to the input of each said multivibrator for triggering said multivibrator at a precomputed time when the return pulse from said target point is to reach the corresponding transducer;
    e. means for generating a chirp waveform having a frequency varying unidirectionally with time, means for connecting said chirp waveform to the second input of all said gate means;
    f. a dispersive transversal filter having a frequency curve opposite to that of said chirp waveform, and means for connecting the output of all said mixer means to said filter.

7. Apparatus in accordance with claim 6 wherein each of said mixer means comprises a double balanced communications type mixer.

8. Apparatus in accordance with claim 6 wherein the output of each said multivibrator is a pulse having a constant width equal to approximately the time duration of said return pulses, respectively, received by said transducers.

9. Apparatus in accordance with claim 6 wherein said means for generating a chirp waveform and said dispersive transversal filter comprise a matched pair of surface wave acoustic delay lines.

10. In an acoustic imaging system wherein echo pulses from many points may be received by an array of transducers, means for correlating the return pulses received by said transducers from only one target point which comprises:
   a. mixer means for each said transducer, each said mixer means having two inputs and one output, a signal line connected from the corresponding transducer to one of said mixer inputs;
   b. gate means for each said mixer means, each said gate means having two inputs and one output, the output of said mixer means connected to one of said gate means inputs;
   c. a one-shot multivibrator for each said gate means, each said multivibrator having its output connected to the other input of its corresponding gate means;
   d. separate trigger means connected to the input of each said multivibrator for triggering said multivibrator at a precomputed time when the return pulse from said target point is to reach the corresponding transducer;
   e. means for generating a chirp waveform having a frequency varying unidirectionally with time, means for connecting said chirp waveform to the second input of all said mixer means;
   f. a dispersive transversal filter having a frequency curve oppostie to that of said chirp waveform, and means for connecting the output of all said gate means to said filter.

11. In an acoustic imaging system wherein echo pulses from many points may be received by an array of transducers, means for correlating the return pulses received by said transducers from only one target point which comprises:
   a. gate means for each said transducer, each said gate means having two inputs and one output, a signal line connected from the corresponding transducer to one of said gate means inputs;
   b. a one-shot multivibrator for each said gate means, each said multivibrator having its output connected to the other input of its corresponding gate means;
   c. separate trigger means connected to the input of each said multivibrator for triggering said multivibrator at a precomputed time when the return pulse from said target point is to reach the corresponding transducer;
   d. mixer means for each said gate means, each said mixer means having two inputs and one output, the output of said gate means connected to one of said mixer inputs;
   e. means for generating a chirp waveform having a frequency varying unidirectionally with time, means for connecting said chirp waveform to the second input of all said mixer means;
   f. a dispersive transversal filter having a frequency curve opposite to that of said chirp waveform, and means for connecting the output of all said mixer means to said filter.

12. In a phased array acoustic imaging system, in combination:
   a. an array of relatively fixed ultrasonic transducers;
   b. an electronic pulser/receiver unit electrically connected to each said transducer;
   c. means for connecting transmit trigger pulses to said pulser/receivers; and
   d. means for correlating return pulses from said pulser/receivers, comprising
      (1) means for generating a chirp signal varying unidirectionally in frequency with time,
      (2) means for generating a gate signal of predetermined width and timing for each said transducer to coincide with the return signal at the respective transducer,
      (3) mixer means for obtaining the product of said return, chirp and gate signals at each of said transducers, and
      (4) means for obtaining the summation of said products simultaneously.

13. Apparatus in accordance with claim 12 wherein said summation means comprises a dispersive transversal filter.

* * * * *